US008198247B2

(12) United States Patent
Boulanger et al.

(10) Patent No.: US 8,198,247 B2
(45) Date of Patent: Jun. 12, 2012

(54) PROCESS FOR AND INTERMEDIATES IN THE PREPARATION OF CANFOSFAMIDE AND ITS SALTS

(75) Inventors: William A. Boulanger, Mahomet, IL (US); Dennis L. Edie, Delmar, NY (US); Ronan Y. Guevel, Villeurbanne (FR); Pedro E. Hernandez Abad, Arroyo, PR (US); R. Jason Herr, Voorheesville, NY (US); Harold Meckler, Delmar, NY (US); Steven R. Schow, Redwood City, CA (US); Pavel E. Zhichkin, Latham, NY (US)

(73) Assignee: Telik, Inc., Palo Alto, CA (US)

( * ) Notice: Subject to any disclaimer, the term of this patent is extended or adjusted under 35 U.S.C. 154(b) by 632 days.

(21) Appl. No.: 11/018,391

(22) Filed: Dec. 21, 2004

(65) Prior Publication Data

US 2006/0135409 A1    Jun. 22, 2006

(51) Int. Cl.
*A61K 38/14*    (2006.01)
(52) U.S. Cl. .................... 514/21.91; 514/47; 514/73
(58) Field of Classification Search .................. None
See application file for complete search history.

(56) References Cited

U.S. PATENT DOCUMENTS

| 5,556,942 | A * | 9/1996 | Kauvar et al. ............. 530/331 |
| 6,417,397 | B1 * | 7/2002 | Goodman et al. ............. 564/123 |
| 6,506,739 | B1 | 1/2003 | Herr et al. |
| 7,192,918 | B2 * | 3/2007 | Schow et al. .................... 514/2 |

FOREIGN PATENT DOCUMENTS

| WO | WO 95/09866 | 4/1995 |
| WO | WO 01/83496 A1 | 11/2001 |

OTHER PUBLICATIONS

McIntyre, et al., Canfosfamide Hydrochloride-Oncolytic-DNA Alkylating Drug, Drugs of th Future, 2004, vol. 28, No. 10, pp. 985-991.*
Chapter 22 Amines, Organic Chemistry 4e Carey Online Learing Center, 2000, pp. 1-4, http://www.mhhe.com/physsci/chemistry/care/student/lc/ch22amines.html, printed Sep. 24, 2007.*
Oxidation of Aniline with Benzoyl Peroxide, Chemistry Comes Alive, 2001, pp. 1-2, http://www.jce.divched.org/JCESoft/CCA/ CCA5/MAIN/1ORGANIC/ORG14/TRAM14/C/0470423/ THUMBS.HTML, Printed Sep. 24, 2007.*
Theodora W. Greene and Peter G.M. Wuts, Chapeter 7 Protection for the Amino Group Protective Groups in Organic Synthesis and Chapter 10 Reactivities, Reagent and Reactivity Charts, Third Edition, 1999, pp. 494-537 and 701-747.*
D.M. Townsend et al. Molecular Cancer Therapeutics. (2002) 1, pp. 1089-1095.*
J.-O. Hoog et al. FEBS Letters. (1982) 138(1), pp. 59-61.*
A.E.P. Adang et al. Biochemical Journal. (1991) 278, pp. 63-68.*
K.-W. Yang et al.Archives of Biochemistry and Biophysics. (2003) 414, pp. 271-278.*
L.M. Shaw and D.A. Newman. Clinical Chemistry. (1979) 25(1), pp. 75-79.*
Townsend et. al. Efficacy of Glutathione S-transferase activated Prodrug in Platinum-resistant Ovarian Cancer Cells, Molecular Cancer Therapeutics, vol. 1 1089-1095 (2002).*
Hoog et. al. Glutathione derivatives as inhibitors of glutaredoxin and ribonucleotide reductase from *Escherichia coli*. FEBS Letters vol. 138, No. 1( Feb 1982).*
Yang et. al. Explaining the inhibition of glyoxylase II by 9-Fluorenylmethoxycarbonyl protected glutathion derivatives. Archives of Biochemistry and Physics. vol. 414 271-278 (2003).*
Amy S. Morgan, et al., "Tumor Efficacy and Bone Marrow-sparing Properties of TER286, a Cytotoxin Activated by Glutathione S-Transferase", Cancer Research 58: 2568-2575, Jun. 15, 1998.
Lilliam A. Rosario, et al., "Cellular Response to a Glutathione *S*-Transferase P1-1 Activated Prodrug", The American Society for Pharmacology and Experimental Therapies, Mol. Pharm. 58:167-174, 2000.
Matthew H. Lyttle, et al., "Isozyme-Specific Glutathione-*S*-Transferase Inhibitors: Design and Synthesis", J. Med Chem. 37: 189-194, 1994.
R. Jason Herr, et al., "An Efficient Synthesis of 2-Hydroxyethyl N,N,N', N'-Tetrakis (2-chloroethyl)phosphorodiamidate", Organic Process Research & Development 5: 442-444, 2001.
Ciaccio P. J., et al.; "Modulation of Detoxification Gene Expression in Human Colon HT29 Cells by Glutathione-S-Transferase Inhibitors", Molecular Pharmacology, Baltimore, MD, vol. 48, No. 4; Oct. 1, 1995, pp. 639-647.
Lyttle, M. H., et al.; "Glutathione-S-Transferase Activates Novel Alkylating Agents"; Journal of Medicinal Chemistry, American Chemical Society; vol. 37, No. 10, 1994; pp. 1501-1507.
McIntyre J. A., et al. ; "Canfosfamide Hydrochloride-Oncolytic-DNA Alkylating Drug"; Drugs of the Future; Barcelona, ES, vol. 29, No. 10; Oct. 10, 2004.

* cited by examiner

*Primary Examiner* — Anish Gupta
*Assistant Examiner* — Jeanette Lieb
(74) *Attorney, Agent, or Firm* — Foley & Lardner LLP

(57) ABSTRACT

A process for and intermediates in the preparation of canfosfamide and its salts. Some of the intermediates have anticancer activity.

2 Claims, 2 Drawing Sheets

PROCESS FOR AND INTERMEDIATES IN THE PREPARATION OF CANFOSFAMIDE AND ITS SALTS

BACKGROUND OF THE INVENTION

1. Field of the Invention

This invention relates to canfosfamide and its salts, and in particular to their preparation and intermediates in their preparation.

2. Description of the Related Art

U.S. Pat. No. 5,556,942 and PCT International Publication No. WO 95/09866 disclose compounds of the formula

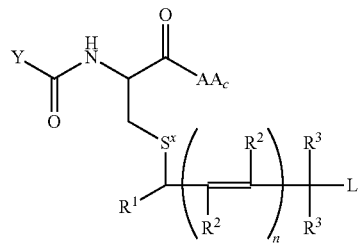

and their amides, esters, and salts, where:

L is an electron withdrawing leaving group;

$S^x$ is —S(=O)—, —S(=O)$_2$—, —S(=NH)—, —S(=O)(=NH)—, —S$^+$(C$_1$-C$_6$ alkyl)-, —Se(=O)—, —Se(=O)$_2$—, —Se(=NH)—, or —Se(=O)(=NH)—, or is —O—C(=O)—, or —HN—C(=O)—;

each $R^1$, $R^2$ and $R^3$ is independently H or a non-interfering substituent;

n is 0, 1 or 2;

Y is selected from the group consisting of

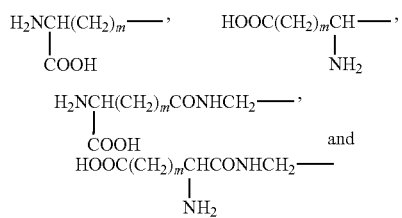

where m is 1 or 2; and

AA$_c$ is an amino acid linked through a peptide bond to the remainder of the compound, and their syntheses.

The compounds are stated to be useful drugs for the selective treatment of target tissues that contain compatible GST isoenzymes, and simultaneously elevate the levels of GM progenitor cells in bone marrow. Disclosed embodiments for L include those that generate a drug that is cytotoxic to unwanted cells, including the phosphoramidate and phosphorodiamidate mustards.

TLK286, identified in those publications as TER 286 and named as γ-glutamyl-α-amino-β-((2-ethyl-N,N,N,N-tetra(2'-chloro)ethylphosphoramidate)sulfonyl)propionyl-(R)-(-)phenylglycine, is one of these compounds. TLK286 is the compound of the formula

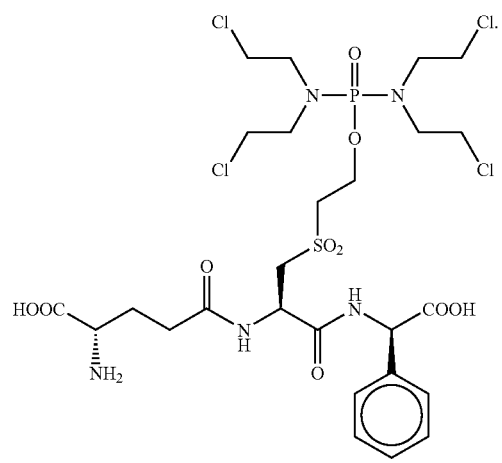

TLK286 as the hydrochloride salt has the United States Adopted Name (USAN) of canfosfamide hydrochloride.

Lyttle et al., *J. Med. Chem.*, 37:1501-1507 (1994), disclose canfosfamide and two analogs, their synthesis, and their interaction with three GST isoenzymes. The synthesis involves the reaction of the unprotected tripeptide (L-γ-glutamyl-L-cysteinyl-2-phenyl-(2R)-glycine in the case of canfosfamide) with a 2-bromoethyl phosphorodiamidate (2-bromoethyl N,N,N',N'-tetrakis(2-chloroethyl)phosphorodiamidate in the case of canfosfamide), followed by oxidation of the resulting thioether with hydrogen peroxide and peracetic acid.

Canfosfamide is an anticancer compound that is activated by the actions of GST P1-1, and by GST A1-1, to release the cytotoxic phosphorodiamidate moiety. Following activation of canfosfamide by GST P1-1, apoptosis is induced through the stress response signaling pathway with the activation of MKK4, JNK, p38 MAP kinase, and caspase 3. In vitro, canfosfamide has been shown to be more potent in the M6709 human colon carcinoma cell line selected for resistance to doxorubicin and the MCF-7 human breast carcinoma cell line selected for resistance to cyclophosphamide, both of which overexpress GST P1-1, than in their parental cell lines; and in murine xenografts of M7609 engineered to have high, medium, and low levels of GST P1-1, the potency of canfosfamide was positively correlated with the level of GST P1-1 (Morgan et al., *Cancer Res.*, 58:2568-2575 (1998)).

Canfosfamide hydrochloride, as a single agent, and in combination with other anticancer agents, is currently being evaluated in multiple clinical trials for the treatment of ovarian, breast, non-small cell lung, and colorectal cancers. It has demonstrated significant single agent antitumor activity and improvement in survival in patients with non-small cell lung cancer and ovarian cancer, and single agent antitumor activity in colorectal and breast cancer. Evidence from in vitro cell culture and tumor biopsies indicates that canfosfamide is non-cross-resistant to platinum, paclitaxel, and doxorubicin (Rosario et al., *Mol. Pharmacol.*, 58:167-174 (2000)), and also to gemcitabine. Patients treated with canfosfamide hydrochloride show a very low incidence of clinically significant hematological toxicity.

Herr et al., *Org. Proc. Res. Dev.*, 5:442-444 (2001), disclose a retrosynthetic approach to canfosfamide from the unprotected tripeptide L-γ-glutamyl-L-cysteinyl-2-phenyl-(2R)-glycine and a 2-(arylsulfonyloxy)ethyl N,N,N',N'-tetrakis(2-chloroethyl)phosphorodiamidate; and the synthesis of the 2-(arylsulfonyloxy)ethyl N,N,N',N'-tetrakis(2-chloroethyl)phosphorodiamidate in three steps from POCl$_3$, passing through 2-hydroxyethyl N,N,N',N'-tetrakis(2-chloroethyl) phosphorodiamidate. U.S. Pat. No. 6,506,739 and PCT International Publication No. WO 01/83496 disclose 2-(substituted)ethyl N,N,N',N'-tetrakis(2-haloethyl) phosphorodiamidates, including 2-hydroxyethyl N,N,N',N'-tetrakis(2-chloroethyl)phosphorodiamidate and 2-(arylsulfonylox)ethyl N,N,N',N'-tetrakis(2-chloroethyl) phosphorodiamidates, such as 2-(4-bromobenzenesulfonyloxy)ethyl N,N,N',N'-tetrakis (2-chloroethyl)phosphorodiamidate.

The disclosures of the documents referred to in this application are incorporated into this application by reference.

SUMMARY OF THE INVENTION

In a first aspect, this invention is compounds of the formula

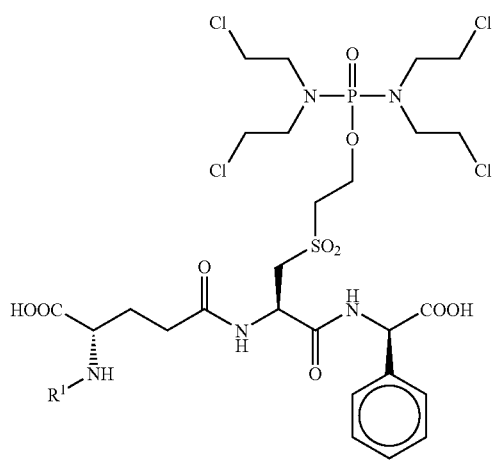

where R¹ is an amine-protecting group,
and their salts.

In a second aspect, this invention is compounds of the formula

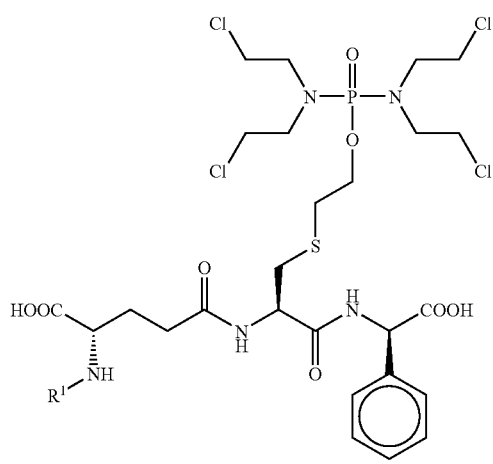

where R¹ is an amine-protecting group,
and their salts.

In a third aspect, this invention is compounds of the formula

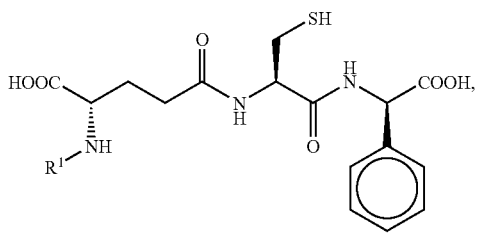

where R¹ is an amine-protecting group,
and their salts.

In a fourth aspect, this invention is compounds of the formula

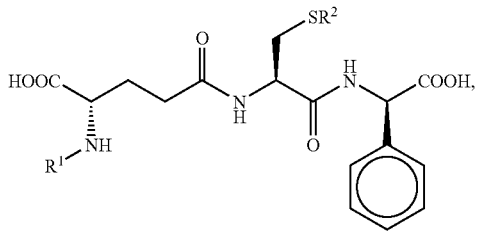

where R¹ is an amine-protecting group, and R² is a sulfur-protecting group,
and their salts.

In a fifth aspect, this invention is methods of preparing canfosfamide or its salt, comprising deprotecting a compound of the first aspect of this invention, optionally followed by forming a salt of canfosfamide.

In a sixth aspect, this invention is methods of preparing compounds of the first aspect of this invention, comprising oxidizing a compound of the second aspect of this invention.

In an seventh aspect, this invention is methods of preparing compounds of the second aspect of this invention, comprising reacting a compound of the third aspect of this invention with a 2-(A-sulfonyloxy)ethyl N,N,N',N'-tetrakis (2-chloroethyl) phosphorodiamidate under basic conditions.

In an eighth aspect, this invention is methods of preparing compounds of the third aspect of this invention, comprising deprotecting the sulfur atom of a compound of the fourth aspect of this invention.

In a ninth aspect, this invention is pharmaceutical compositions comprising a compound of the first aspect of this invention, methods of treating cancer by administering a compound of the first aspect of this invention, and compounds of the first aspect of this invention for the treatment of cancer and for use in the manufacture of medicaments for the treatment of cancer.

Preferred embodiments of this invention are characterized by the specification of this application as filed.

DETAILED DESCRIPTION OF THE INVENTION

Definitions

Figure 1:
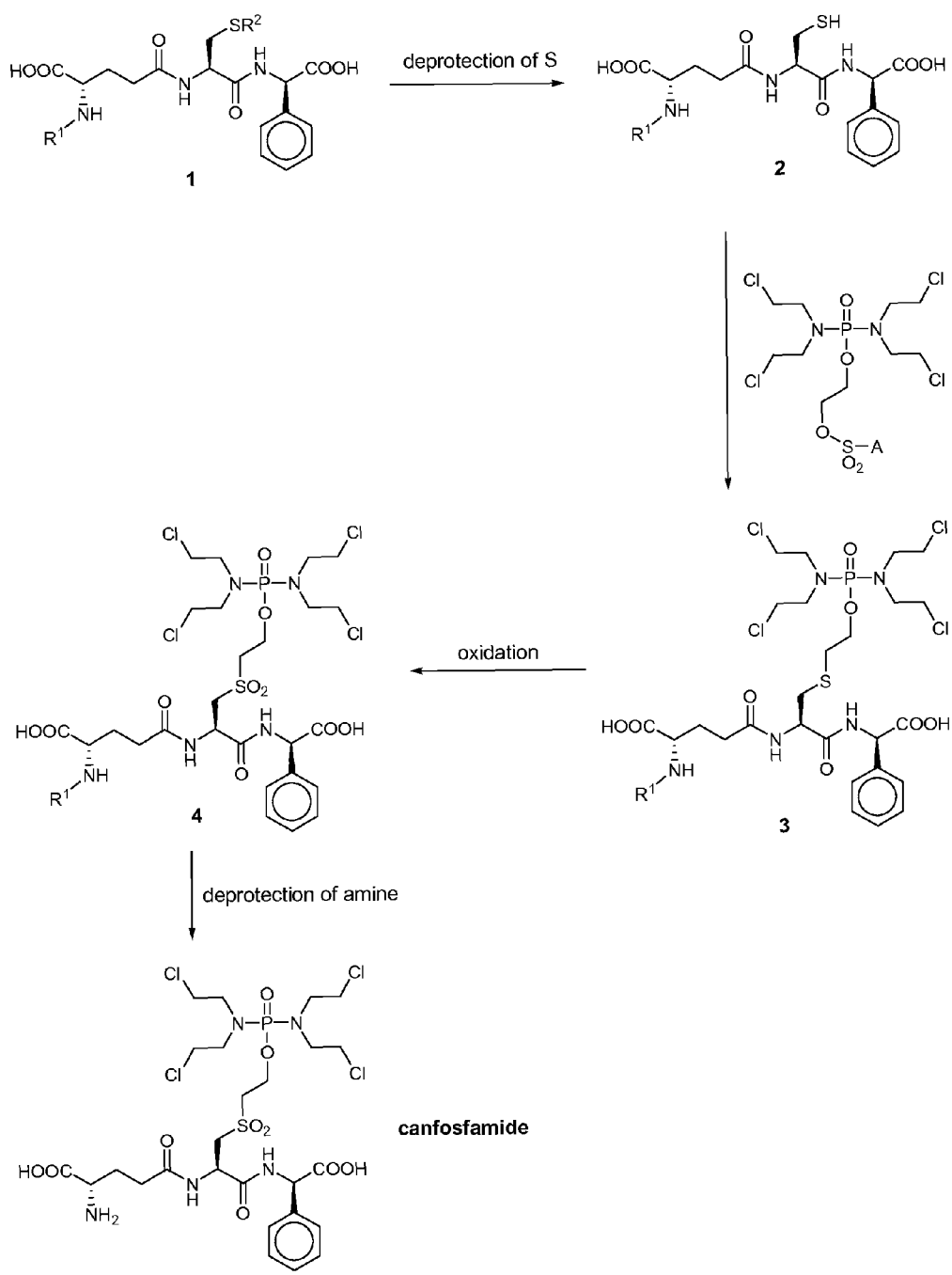
FIG. 1 is a reaction scheme illustrating the process of this invention.

"Canfosfamide" is the compound of the formula:

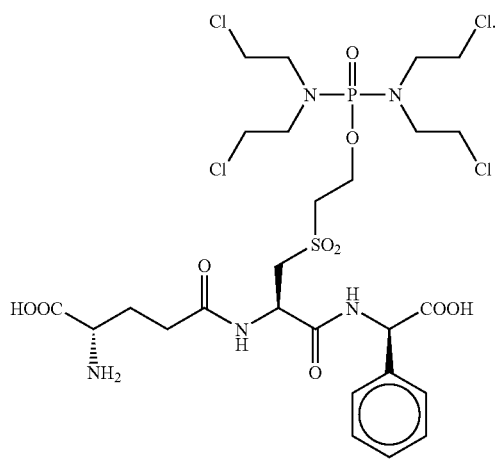

It has the CAS name L-γ-glutamyl-3-[[2-[[bis[bis(2-chloroethyl)amino]phosphinyl]oxy]ethyl]sulfonyl]-L-alanyl-2-phenyl-(2R)-glycine.

Suitable salts (see Berge et al., *J. Pharm. Sci.*, 66:1 (1971) for a nonexclusive list) of canfosfamide and the compounds of this invention are those formed when inorganic bases (e.g. sodium, potassium, and calcium hydroxide) or organic bases (e.g. ethanolamine, diethanolamine, triethanolamine, ethylenediamine, tromethamine, N-methylglucamine) react with the carboxyl groups, and those formed when inorganic acids (e.g hydrochloric, hydrobromic, sulfuric, nitric, and chlorosulfonic acids) or organic acids (e.g. acetic, propionic, oxalic, malic, maleic, malonic, fumaric, or tartaric acids, and alkane- or arenesulfonic acids such as methanesulfonic, ethanesulfonic, benzenesulfonic, substituted benzenesulfonic such as chlorobenzenesulfonic and toluenesulfonic, naphthalenesulfonic and substituted naphthalenesulfonic, naphthalenedisulfonic and substituted naphthalenedisulfonic, and camphorsulfonic acids) react to form acid addition salts of the amine groups, of canfosfamide and the compounds. Such salts are preferably formed with pharmaceutically acceptable acids and bases. A suitable salt for canfosfamide is the hydrochloride salt.

An "amine-protecting group" is a group capable of protecting the glutamyl α-amine group of L-γ-glutamyl-L-cysteinyl-2-phenyl-(2R)-glycine during the synthesis of the amine-protected canfosfamide, and subsequently removable without affecting the remainder of the canfosfamide molecule. A "catalytically removable amine-protecting group" is an amine-protecting group that is removable by catalytic reduction or isomerization. Common such groups are urethane-forming groups containing a benzylic or allylic carbon atom. Examples of catalytically removable amine-protecting groups suitable for use in this invention are (optionally substituted benzyl)oxycarbonyl, conveniently removable by catalytic hydrogenolysis, and (optionally substituted allyl)oxycarbonyl groups, conveniently removable by catalytic isomerization. A particularly suitable catalytically removable amine-protecting group is benzyloxycarbonyl.

An "(optionally substituted benzyl)oxycarbonyl" includes benzyloxycarbonyl and benzyloxycarbonyl substituted on the benzene ring with one or two, typically one, electron-withdrawing substituents, such as halo (typically chloro or bromo), nitro, cyano, and trifluoromethyl. Examples of (optionally substituted benzyl)oxycarbonyl include benzyloxycarbonyl, halo-benzyloxycarbonyls such as 2- and 4-bromobenzyloxycarbonyl, 2-, 3-, and 4-chlorobenzyloxycarbonyl, and 2,4-dichlorobenzyloxycarbonyl, 2-, 3-, and 4-nitrobenzyloxycarbonyl, 4-cyanobenzyloxycarbonyl, and the like.

An "(optionally substituted allyl)oxycarbonyl" includes allyloxycarbonyl and allyloxycarbonyl substituted with an electron-withdrawing substituent (such as phenyl optionally substituted with one or two, typically one, electron-withdrawing substituents, or pyridyl) on the 3-position of the group, and 1-isopropylallyloxycarbonyl. Examples of (optionally substituted allyl)oxycarbonyl include allyloxycarbonyl, cinnamyloxycarbonyl, 4-nitrocinnamyloxycarbonyl, 3-(3'-pyridyl)allyloxycarbonyl, and 1-isopropylallyloxycarbonyl.

A sulfur-protecting group" is a group capable of protecting the sulfur atom of L-γ-glutamyl-L-cysteinyl-2-phenyl-(2R)-glycine during the synthesis of compounds of the fourth aspect of this invention, and subsequently removable without affecting the remainder of the molecule of the corresponding compound of the third aspect of this invention (including the amine-protecting group). An "acidolytically removable sulfur-protecting group" is a sulfur-protecting group that is removable by acidolysis. Common such groups are (optionally substituted phenyl)-substituted methyl groups. Examples of acidolytically removable sulfur-protecting groups suitable for use in this invention are triphenylmethyl in which one or more of the benzene rings are optionally substituted with one or more, typically one, electron-donating substituents, such as methoxy, e.g. (4-methoxyphenyl)diphenylmethyl and bis (4-methoxyphenyl)phenymethyl; diphenylmethyl in which one or more of the benzene rings are optionally substituted with one or more, typically one, electron-donating substituents, such as methoxy, e.g. (4-methoxyphenyl)phenylmethyl and bis(4-methoxyphenyl)methyl; diphenylmethyl analogs such as 9H-xanthen-9-yl, 2-methoxy-9H-xanthen-9-yl, 5H-dibenzo[a,d]cyclohepten-5-yl, and 10,11-dihydro-5H-dibenzo[a,d]cyclohepten-5-yl; and benzyl substituted with two or more electron-donating substituents, such as methoxy, e.g. 2,4-dimethoxybenzyl and 2,4,6-trimethoxybenzyl. A particularly suitable acidolytically removable sulfur-protecting group is the triphenylmethyl group.

Amine-protecting groups, including catalytically removable amine-protecting groups, and sulfur-protecting groups, including acidolytically removable sulfur-protecting groups, are well known in the field of organic synthesis and particularly peptide synthesis. Suitable such groups, and the conditions for their removal, are described in books such as *Synthesis of Peptides and Peptidomimetics, Workbench edition*, M. Goodman, ed., Georg Thieme Verlag, Stuttgart, Germany, 2004, and *Protective groups in organic synthesis*, 3 ed., T. W. Greene and P. G. M. Wuts, eds., John Wiley & Sons, Inc., New York, N.Y., U.S.A, 1999, and will be well known to a person of ordinary skill in the art.

Figure 2:
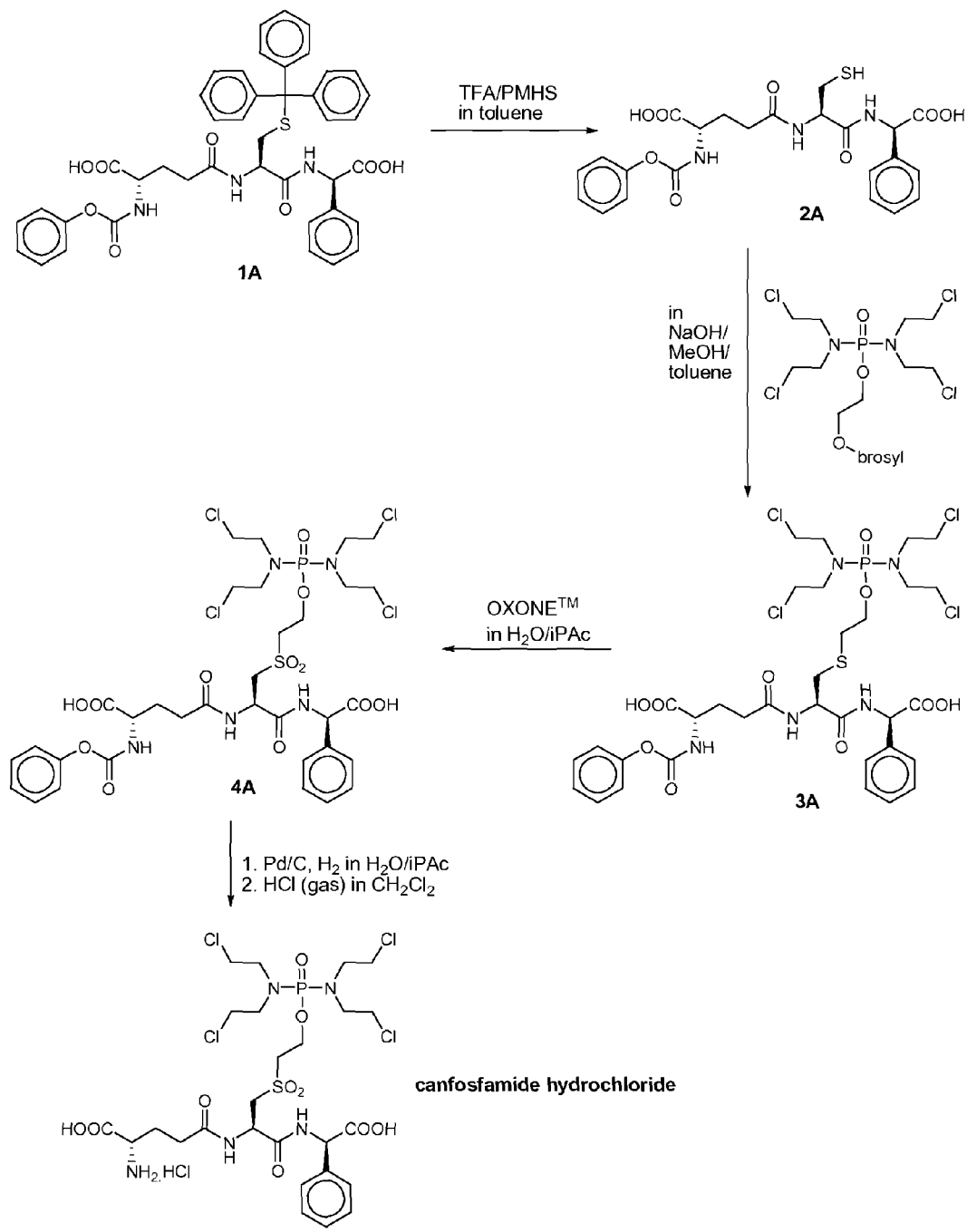
FIG. 2 is a reaction scheme illustrating the process of this invention to prepare preferred compounds.

Because the compounds of the fourth aspect of this invention contain both an amine-protecting group, especially a catalytically removable amine-protecting group, and a sulfur-protecting group, especially an acidolytically removable sulfur-protecting group, and the eighth aspect of this invention involves deprotecting the sulfur atom of these compounds while leaving the amine-protecting group in place, a person of ordinary skill in the art will understand that the "amine-protecting group" and "sulfur-protecting group" are not chosen independently and their definitions are to be interpreted in the context of their description in the application and the reaction sequence shown in FIGS. 1 and 2; and that the amine-protecting group and the sulfur-protecting group are to be selected so that the sulfur-protecting group can be removed under conditions that leave the amine-protecting group intact. Such a person will have no difficulty, considering the information in this application and the ordinary skill in the art, in selecting suitable amine-protecting and sulfur-protecting groups and removal conditions.

A "2-(A-sulfonyloxy)ethyl N,N,N',N'-tetrakis(2-chloroethyl)phosphorodiamidate" is a compound of the formula

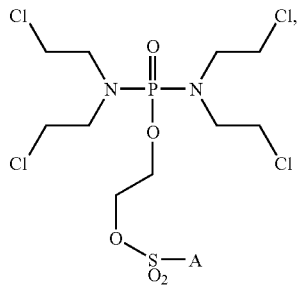

where A is optionally substituted aryl, optionally substituted aryl, optionally substituted heteroaryl, optionally substituted aralkyl, or optionally substituted heteroaralkyl. Thus A includes $C_{1-4}$ alkyl, optionally substituted with 1 to 3 halogen atoms and further optionally substituted with nitro or cyano; $C_{6-10}$ aryl such as phenyl and naphthyl, especially phenyl, optionally substituted with 1 to 3 groups selected from halogen, nitro, cyano, and $C_{1-2}$ alkyl optionally substituted with 1 to 3 halogen atoms; $C_{5-10}$ heteroaryl such as furyl, thienyl, pyrrolyl, pyridinyl, pyrazinyl, pyrimidinyl, optionally substituted with 1 to 3 groups selected from halogen, nitro, cyano, and $C_{1-2}$ alkyl optionally substituted with 1 to 3 halogen atoms; and $C_{6-10}$, aryl-$C_{1-2}$ alkyl and $C_{5-10}$ heteroaryl-$C_{1-2}$ alkyl, each optionally substituted on the aryl or heteroaryl group with 1 to 3 groups selected from halogen, nitro, cyano, and $C_{1-2}$ alkyl optionally substituted with 1 to 3 halogen atoms, and on the alkyl group with 1 to 3 halogen atoms. Examples of A groups include methyl, trifluoromethyl, phenyl, 4-tolyl, 4-nitrophenyl, and 4-halophenyl such as 4-chlorophenyl and 4-bromophenyl.

"Brosyl" means 4-bromobenzenesulfonyl.

A "therapeutically effective amount" means the amount that, when administered to a mammal, especially a human, for treating a cancer, is sufficient to effect treatment for the cancer. "Treating" or "treatment" of a cancer in a mammal includes one or more of:

(1) inhibiting growth of the cancer, i.e., arresting its development, (2) preventing spread of the cancer, i.e. preventing metastases, (3) relieving the cancer, i.e., causing regression of the cancer, (4) preventing recurrence of the cancer, and (5) palliating symptoms of the cancer.

If a compound of the first aspect of this invention is administered as part of a combination therapy with one or more other anticancer agents or radiotherapy, the "therapeutically effective amount" may be lower than the amount that would be therapeutically effective if the compound were administered alone.

The compounds of this invention and their preparation

The compounds of the first aspect of this invention are compounds of the formula

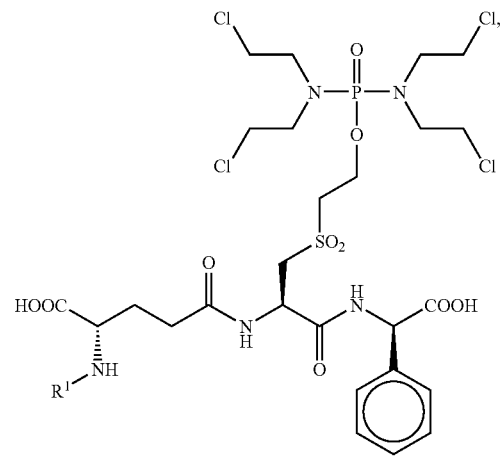

where $R^1$ is an amine-protecting group, especially a catalytically removable amine-protecting group, and their salts (compounds 4).

Particular compounds of the first aspect of this invention are compounds where $R^1$ is an (optionally substituted benzyl)oxycarbonyl such as benzyloxycarbonyl, a halo-benzyloxycarbonyl such as 2- or 4-bromobenzyloxycarbonyl, 2-, 3-, or 4-chlorobenzyloxycarbonyl, or 2,4-dichlorobenzyloxycarbonyl, 2-, 3-, or 4-nitrobenzyloxycarbonyl, or 4-cyanobenzyloxycarbonyl; or an (optionally substituted allyl)oxycarbonyl such as allyloxycarbonyl, cinnamyloxycarbonyl, 4-nitrocinnamyloxycarbonyl, 3-(3'-pyridyl)allyloxycarbonyl, or 1-isopropylallyloxycarbonyl. Compounds of special interest are compounds where $R^1$ is benzyloxycarbonyl, i.e. N-α-(benzyloxycarbonyl)-L-γ-glutamyl-3-[[2-[[bis[bis(2-chloroethyl)amino]phosphinyl]oxy]ethyl]sulfonyl]-L-alanyl-2-phenyl-(2R)-glycine or a salt, especially a pharmaceutically acceptable salt.

The compounds of the second aspect of this invention are compounds of the formula

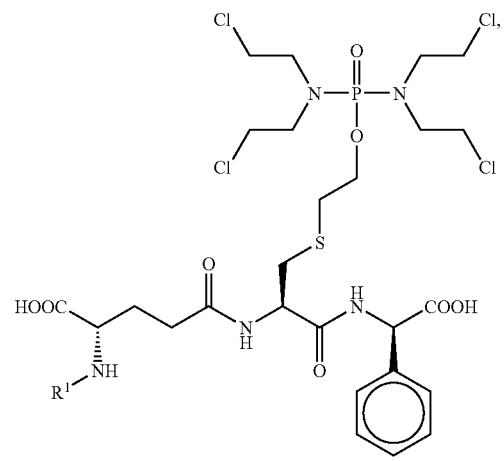

where $R^1$ is an amine-protecting group, especially a catalytically removable amine-protecting group, and their salts (compounds 3).

Particular compounds of the second aspect of this invention are compounds where $R^1$ is an (optionally substituted benzyl)oxycarbonyl such as benzyloxycarbonyl, a halo-benzyloxycarbonyl such as 2- or 4-bromobenzyloxycarbonyl, 2-, 3-, or 4-chlorobenzyloxycarbonyl, or 2,4-dichlorobenzyloxycarbonyl, 2-, 3-, or 4-nitrobenzyloxycarbonyl, or 4-cyanobenzyloxycarbonyl; or an (optionally substituted allyl)oxycarbonyl such as allyloxycarbonyl, cinnamyloxycarbonyl, 4-nitrocinnamyloxycarbonyl, 3-(3'-pyridyl)allyloxycarbonyl, or 1-isopropylallyloxycarbonyl. Compounds of special interest are compounds where $R^1$ is benzyloxycarbonyl, i.e. N-α-(benzyloxycarbonyl)-L-γ-glutamyl-3-[[2-[[bis[bis(2-chloroethyl)amino]phosphinyl]oxy]ethyl]thio]-L-alanyl-2-phenyl-(2R)-glycine or a salt.

The compounds of the third aspect of this invention are compounds of the formula

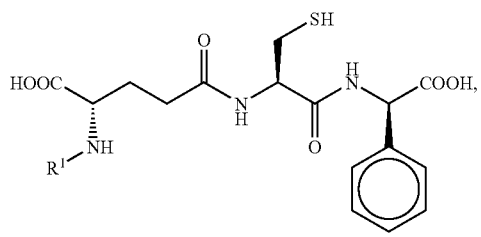

where $R^1$ is an amine-protecting group, especially a catalytically removable amine-protecting group, and their salts (compounds 2).

Particular compounds of the third aspect of this invention are compounds where $R^1$ is an (optionally substituted benzyl)oxycarbonyl such as benzyloxycarbonyl, a halo-benzyloxycarbonyl such as 2- or 4-bromobenzyloxycarbonyl, 2-, 3-, or 4-chlorobenzyloxycarbonyl, or 2,4-dichlorobenzyloxycarbonyl, 2-, 3-, or 4-nitrobenzyloxycarbonyl, or 4-cyanobenzyloxycarbonyl; or an (optionally substituted allyl)oxycarbonyl such as allyloxycarbonyl, cinnamyloxycarbonyl, 4-nitrocinnamyloxycarbonyl, 3-(3'-pyridyl)allyloxycarbonyl, or 1-isopropylallyloxycarbonyl. Compounds of special interest are compounds where $R^1$ is benzyloxycarbonyl, i.e. N-α-(benzyloxycarbonyl)-L-γ-glutamyl-L-cysteinyl-2-phenyl-(2R)-glycine or a salt.

The compounds of the fourth aspect of this invention are compounds of the formula

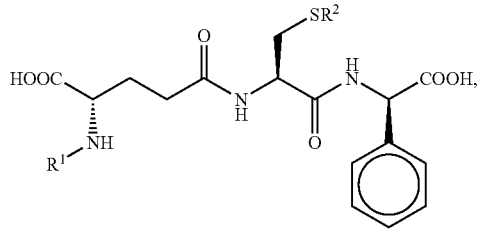

where $R^1$ is an amine-protecting group, especially a catalytically removable amine-protecting group, and $R^2$ is a sulfur-protecting group, especially an acidolytically removable sulfur-protecting group, and their salts (compounds 1).

Particular compounds of the fourth aspect of this invention are compounds where $R^1$ is an (optionally substituted benzyl)oxycarbonyl such as benzyloxycarbonyl, a halo-benzyloxycarbonyl such as 2- or 4-bromobenzyloxycarbonyl, 2-, 3-, or 4-chlorobenzyloxycarbonyl, or 2,4-dichlorobenzyloxycarbonyl, 2-, 3-, or 4-nitrobenzyloxycarbonyl, or 4-cyanobenzyloxycarbonyl; or an (optionally substituted allyl)oxycarbonyl such as allyloxycarbonyl, cinnamyloxycarbonyl, 4-nitrocinnamyloxycarbonyl, 3-(3'-pyridyl)allyloxycarbonyl, or 1-isopropylallyloxycarbonyl. Compounds of special interest are compounds where $R^1$ is benzyloxycarbonyl.

Further particular compounds of the fourth aspect of this invention are compounds where $R^2$ is an (optionally substituted phenyl)-substituted methyl such as triphenylmethyl, 4-methoxyphenyl)diphenylmethyl, bis(4-methoxyphenyl)phenylmethyl, diphenylmethyl, 4-methoxyphenyl)phenylmethyl, bis(4-methoxyphenyl)methyl, 9H-xanthen-9-yl, 2-methoxy-9H-xanthen-9-yl, 5H-dibenzo[a,d]cyclohepten-5-yl, 10,11-dihydro-5H-dibenzo[a,d]cyclohepten-5-yl, 2,4-dimethoxybenzyl, or 2,4,6-trimethoxybenzyl. Compounds of special interest are compounds where $R^2$ is triphenylmethyl.

A compound of the fourth aspect of this invention that is of special interest is the compound where $R^1$ is benzyloxycarbonyl and $R^2$ is triphenylmethyl, i.e. N-α-(benzyloxycarbonyl)-L-γ-glutamyl-S-triphenylmethyl-L-cysteinyl-2-phenyl-(2R)-glycine or a salt.

The preparation of the compounds of this invention and canfosfamide and its salts by the process of this invention is illustrated in FIG. 1.

In this application, the naming of a solvent in a process step is not intended to mean that the solvent is necessarily used alone: the solvent may be used with one or more co-solvents provided that the properties of any solvent mixture are determined primarily by the named solvent.

In the first step, the sulfur atom of compound 1 is deprotected to give compound 2.

Compound 1 may be deprotected by any method suitable for removal of the sulfur-protecting group that does not also remove the amine-protecting group. When the sulfur-protecting group is an acidolytically removable sulfur-protecting group, compound 1 is conveniently deprotected by acidolysis.

Typically, compound 1 is dissolved in an acid that is strong enough to remove the acidolytically removable sulfur-protecting group but not strong enough to remove the catalytically removable amine-protecting group, optionally in the presence of a scavenger. Suitable such acids include trifluoroacetic acid and other strong acids such as trifluoromethanesulfonic acid, optionally in the presence of a cosolvent such as dichloromethane; suitable scavengers include aromatic ethers and sulfides such as anisole and thioanisole, phenols such as cresol, and, most efficiently, silanes including trialkylsilanes such as triethylsilane and triisopropylsilane and silane polymers such as poly(methylhydrosiloxane); and a particularly suitable deprotection reagent is trifluoroacetic acid in the presence of poly(methylhydrosiloxane). Compound 2 can be isolated from the reaction mixture by addition of an anti-solvent, for example an aprotic non-polar solvent such as a hydrocarbon or an ether, and a particularly suitable anti-solvent is a mixture of heptane and methyl tert-butyl ether.

In the second step, the thiolate anion of compound 2 is alkylated with a 2-(A-sulfonyloxy)ethyl N,N,N',N'-tetrakis (2-chloroethyl)phosphorodiamidate to prepare compound 3.

Typically, compound 2 is dissolved in a solution of a strong base (e.g. an alkali metal or alkaline earth metal hydroxide, carbonate, phosphate, or alkoxide, or ammonium hydroxide; or an organic amine base such as tetramethylguanidine, DBU-1,8-diazabicyclo[5.4.0]undec-7-ene, and the like; especially an alkali metal hydroxide) in a suitable solvent (e.g. a $C_{1-6}$ alkanol, a diol such as 1,2-ethanediol or 1,3-propanediol, an ether such as 2-methoxyethanol, 1,2-dimethoxyethane, or tetrahydrofuran, and the like; especially a $C_{1-3}$ alkanol such as methanol) to form the thiolate anion, the phosphorodiamidate is added (typically in excess, for example an excess of at least 1.5-fold, especially at least 2-fold, for example about 2.5-fold, over compound 2), and the reaction mixture is held at an appropriate temperature and time until completion. If the phosphorodiamidate is used in solution in a non-polar aprotic solvent (e.g. an aromatic hydrocarbon such as toluene), on completion of the reaction forming compound 3, the reaction mixture is neutralized, and the aqueous and non-aqueous phases separated to remove unreacted phosphorodiamidate starting material. The lower alkanol is then removed from the aqueous phase and the aqueous phase extracted with a non-polar aprotic solvent (e.g. an ester such as isopropyl acetate) to remove more unreacted phosphorodiamidate starting material. The pH of the aqueous phase is then lowered further, and compound 3 is extracted into a non-polar aprotic solvent. Compound 3 can be isolated from the solution by removal of the solvent; but if the solvent is a suitable solvent for the third step of the process, then compound 3 can be carried into that third step in solution.

In the third step, the sulfur atom of compound 3 is oxidized to prepare compound 4.

Typically, compound 3 is dissolved in a suitable solvent, an oxidizing agent is added, and the reaction mixture is held at a sufficient time and sufficient temperature to complete the oxidation. Suitable solvent/oxidant combinations include $C_{2-3}$ alkanoic acid/hydrogen peroxide/peroxyalkanoic acid combinations such as acetic acid/peroxyacetic acid and acetic acid/hydrogen peroxide/peroxyacetic acid, and the use of $C_{2-3}$ peroxyalkanoic acids or peroxytrifluoroacetic acid as both solvent and oxidant. After quenching excess oxidant with a reagent such as dimethyl sulfide if desired, compound 4 is isolated simply by concentration. Particularly suitable solvent/oxidant combinations include combinations where the oxidation takes place in a biphasic system, with compound 3 dissolved in a non-polar aprotic solvent such as an ester (e.g. isopropyl acetate) and the oxidant being in aqueous solution. Suitable oxidants for these biphasic oxidations include borates and peroxy compounds such as perborates and persulfates, e.g. ammonium, sodium, or potassium persulfate, and a particularly suitable oxidant is potassium monopersulfate, such as OXONE™ (2 $KHSO_5 \cdot KHSO_4 \cdot K_2SO_4$). After separation of the aqueous and non-aqueous phases, and optional washing of the non-aqueous phase to ensure complete removal of any oxidant, compound 4 is isolated from the non-aqueous phase by concentration.

In the fourth step, the amine group of compound 4 is deprotected to prepare canfosfamide, optionally followed by forming an acid addition salt of canfosfamide.

Compound 4 may be deprotected by any method suitable for removal of the amine-protecting group that does not also affect the remainder of the canfosfamide molecule. When the amine-protecting group is a catalytically removable amine-protecting group, compound 4 is conveniently deprotected by catalytic reduction or isomerization.

For catalytic reduction, typically, compound 4 is dissolved in a suitable solvent such as a $C_{1-4}$ alkanol, or a polar protic solvent, or in a non-polar aprotic solvent, especially in the presence of water, e.g. isopropyl acetate in the presence of water, and contacted with hydrogen or a hydrogen donor such as cyclohexene or 1,4-cyclohexadiene in the presence of a reduction catalyst, typically a palladium catalyst such as palladium black, palladium on barium sulfate, and palladium on carbon. After removal of the catalyst, the canfosfamide is conveniently isolated as an acid addition salt by addition of a solvent that will become an anti-solvent for the salt, such as an aprotic solvent, e.g. a hydrocarbon or halogenated hydrocarbon such as dichloromethane, followed by addition of the acid chosen to form the salt, especially in the form of the anhydrous acid alone or in an aprotic solvent, e.g. hydrogen chloride gas. Further anti-solvent for the salt, e.g. ethers such as diethyl ether, methyl tert-butyl ether, and tetrahydrofuran, especially methyl tert-butyl ether, may be added if necessary or desired. For catalytic isomerization, a zerovalent palladium complex such as tetrakis(triphenylphosphine)palladium(0) is used, typically in the presence of a nucleophilic allyl group scavenger such as a secondary amine. The canfosfamide is isolated, typically as an acid addition salt, in a suitable manner.

Uses of the Compounds and Process

The compounds of the first, second, third, and fourth aspects of this invention (compounds of formulae 4, 3, 2, and 1, respectively and the process steps of the fifth, sixth, seventh, and eighth aspects of this invention are useful in the preparation of the known anticancer agent canfosfamide and its salts.

In addition, the compounds of the first aspect of this invention are also active cytotoxic agents. They are therefore useful in the treatment of cancers, especially cancers of types that are treatable with canfosfamide and its salts. These cancers include mammalian cancers, especially human cancers. Cancers that are particularly treatable are cancers with sensitivity to inducers of apoptosis, and more specifically those cancers that express or, particularly, overexpress GST P1-1. Cancers that express or overexpress GST P1-1 when treated with other anticancer therapies (i.e. those not compounds of the first aspect of this invention) are also especially treatable with compounds of the first aspect of this invention when used in combination with the other anticancer therapy. Combination chemotherapy of this type is described for canfosfamide and its analogs in US Patent Application Publication No. US 2004/0138140 and PCT International Publication No. WO 2004/045593. Such cancers include cancers of the brain, breast, bladder, cervix, colon and rectum, esophagus, head and neck, kidney, lung, liver, ovary, pancreas, prostate, and stomach; leukemias such as ALL, AML, AMML, CLL, CML, CMML, and hairy cell leukemia; Hodgkin's and non-Hodgkin's lymphomas; mesotheliomas, multiple myeloma; and sarcomas of bone and soft tissue. Cancers particularly treatable with compounds of the first embodiment of this invention include breast, ovarian, colorectal, and non-small cell lung cancers.

The ninth aspect of this invention is pharmaceutical compositions comprising a compound of the formula

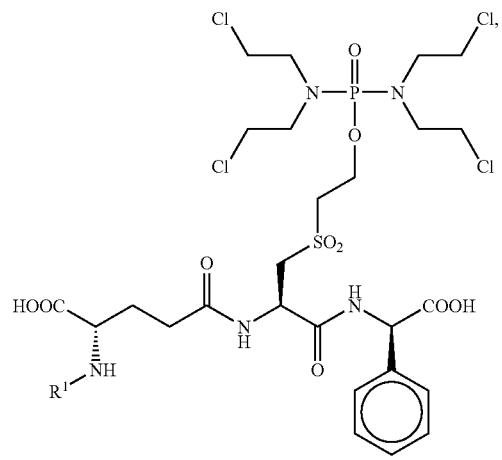

where R¹ is a catalytically removable amine-protecting group, and their salts, methods of treating cancer by administering these compounds, typically in a therapeutically effective amount, and the use of these compounds for the treatment of cancer and for the manufacture of medicaments for the treatment of cancer.

The compounds may be administered by any route suitable to the subject being treated and the nature of the subject's condition. Routes of administration include, but are not limited to, administration by injection, including intravenous, intraperitoneal, intramuscular, and subcutaneous injection, by transmucosal or transdermal delivery, through topical applications, nasal spray, suppository and the like or may be administered orally. Pharmaceutical compositions containing these compounds may optionally be liposomal formulations, emulsions, formulations designed to administer the drug across mucosal membranes or transdermal formulations. Suitable formulations for each of these methods of administration may be found, for example, in *Remington: The Science and Practice of Pharmacy*, 20 ed., A. Gennaro, ed., Lippincott Williams & Wilkins, Philadelphia, Pa., U.S.A., 2003. Typical compositions will be either oral or solutions for intravenous infusion and will contain the compound and typically will also contain one or more pharmaceutically acceptable excipients. Typical dosage forms will be tablets, solutions for intravenous infusion, and lyophilized powders for reconstitution as solutions for intravenous infusion.

A therapeutically effective amount of a compound of the first aspect of this invention is about 50-3000 mg/m² body surface area, especially 500-1500 mg/m². Administration may be at 1-35 day intervals; for example, about 500-1000 mg/m² at 1-5 week intervals, especially at 1, 2, 3, or 4 week intervals, or at higher frequencies including as frequently as once/day for several (e.g. 5 or 7) days, with the administration repeated every 2, 3, or 4 weeks, or constant infusion for a period of 6-72 hours, also with the administration repeated every 2, 3, or 4 weeks; and such flexibility of administration will readily enable combination therapy with other anticancer therapies.

EXAMPLES

The following examples show the preparation of the compounds of this invention and canfosfamide hydrochloride by the process of this invention, and the utility of the compounds of the first aspect of this invention as anticancer agents.

FIG. 2 shows the preparation of preferred compounds of this invention and canfosfamide hydrochloride by the process of this invention. The preparation of N-α(benzyloxycarbonyl)-L-γ-glutamyl-S-triphenylmethyl-L-cysteinyl-2-phenyl-(2R)-glycine, compound 1A, is not shown in FIG. 2, as it will depend on the nature of the protection of its precursor compound, but a process from O-α-benzyl-N-α-benzyloxycarbonyl)-L-γ-glutamyl-S-triphenylmethyl-L-cysteinyl-2-phenyl-(2R)-glycine is described in Example 1 below.

O-α-benzyl-N-α-(benzyloxycarbonyl)-L-γ-glutamyl-S-triphenylmethyl-L-cysteinyl-2-phenyl-(2R)-glycine may be prepared by standard methods of peptide synthesis. A convenient synthesis, using the readily available starting materials N-α-(benzyloxycarbonyl)-L-γ-glutamic acid α-benzyl ester, S-triphenylmethyl-L-cysteine, and D-phenylglycine, is as follows. N-α-(benzyloxycarbonyl)-L-γ-glutamic acid α-benzyl ester is activated as the N-hydroxysuccinimide ester by reaction with N-hydroxysuccinimide and dicyclohexylcarbodiimide in anhydrous 1,4-dioxane. The N-α-(benzyloxycarbonyl)-L-γ-glutamic acid α-benzyl ester γ-N-hydroxysuccinimide ester is dissolved in anhydrous tetrahydrofuran, and added to a solution of S-triphenylmethyl-L-cysteine and triethylamine in water to give O-α-benzyl-N-α-(benzyloxycarbonyl)-L-γ-glutamyl-S-triphenylmethyl-L-cysteine. This is activated as the N-hydroxysuccinimide ester and coupled with D-phenylglycine in the same way as for the γ-glutamine-cysteine coupling to give the desired O-α-benzyl-N-α-(benzyloxycarbonyl)-L-γ-glutamyl-S-triphenylmethyl-L-cysteinyl-2-phenyl (2R)-glycine.

Similar methods but using different activating groups or methods to activate the γ-carboxyl group of the glutamic acid and/or the cysteine carboxyl group for the coupling may also be used; as may methods in which the cysteine-phenylglycine coupling is performed first, followed by coupling of the resulting S-triphenylmethyl-L-cysteinyl-2-phenyl-(2R)-glycine with the N-α-(benzyloxycarbonyl)-L-γ-glutamic acid α-benzyl ester. Other protection of the α-carboxyl group of the N-α-(benzyloxycarbonyl)-L-γ-glutamic acid also may be used provided the α-carboxyl group ultimately can be deprotected while leaving the remainder of the N-α-(benzyloxycarbonyl)-L-γ-glutamyl-S-triphenylmethyl-L-cysteinyl-2-phenyl-(2R)-glycine molecule intact.

Example 1

Preparation of Canfosfamide Hydrochloride

N-α-(benzyloxycarbonyl)-L-γ-glutamyl-S-triphenylmethyl-L-cysteinyl-2-phenyl-(2R)-glycine, 1A A 5-L, three-neck, round-bottom flask, equipped with an overhead mechanical stirrer, a thermometer, and a 2-L pressure-equalizing addition funnel, was charged with O-α-benzyl-N-α-(benzyloxycarbonyl)-L-γ-glutamyl-S-triphenylmethyl-L-cysteinyl-2-phenyl-(2R)-glycine (500 g, 590 mmol) and methanol (1 L). The stirrer was set to agitate at a moderate rate, to provide a clear amber solution, and an aqueous sodium hydroxide solution (1.2 L, 1 M, 1.2 mol) was added over 20 minutes. During this time, the addition caused an exothermic heating of the reaction mixture, increasing the internal reaction temperature to 35° C., and this temperature was maintained throughout the addition. Solids began to precipitate but redissolved by the end of the addition. The reaction mixture was then cooled to room temperature and stirred for 90 minutes, then the methanol was removed under reduced pressure on a rotary evaporator (40 mbar, final bath temperature 35° C.) to provide an aqueous solution of the disodium salt of N-α-(benzyloxycarbonyl)-L-γ-glutamyl-S-triphenylmethyl-L-cysteinyl-2-phenyl-(2R)-glycine. The mixture was charged into a 5-L, three-neck, round-bottom flask equipped with an overhead mechanical stirrer, a thermometer, and a 2-L pressure-equalizing addition funnel, and then diluted with water (1 L). The mixture was cooled to 0° C. using an ice/water bath, and aqueous hydrochloric acid solution (1.3 L, 1 M, 1.3 mol) was added over 20 minutes. During this time, the addition caused solids to precipitate, and the mixture reached a final pH of 4. The resulting slurry was stirred for 30 minutes at 0° C. and the precipitate collected by vacuum filtration and washed with water (1 L). The precipitate was dissolved in dichloromethane (3 L) and the resulting solution was transferred to a 5-L separatory funnel. The aqueous fraction was removed and the organic phase was washed with water (2×1 L), saturated aqueous sodium chloride (1 L), and dried over anhydrous sodium sulfate (100 g). After clarification, the solvent was removed under reduced pressure (40 mbar, 35° C.) on a rotary evaporator to produce an amber foam. The solid product was further dried overnight (40 mbar, 40° C.) to give N-α-(benzyloxycarbonyl)-L-γ-glutamyl-S-triphenylmethyl-L-cysteinyl-2-phenyl-(2R)-glycine, 1A, as an off-white powder (400 g, 89% yield). TLC analysis showed one spot ($R_f$=0.50, silica gel, 1:4 methanol/chloroform). The proton NMR spectrum (DMSO-$d_6$) was consistent with the proposed structure. HPLC analysis showed one major peak (RT=22.1 minutes; 20:80 acetonitrile/0.1 M aqueous $NH_4H_2PO_4$ to 80:20 acetonitrile/0.1 M aqueous $NH_4H_2PO_4$ over 30 minutes; flow=1.0 mL/minute; detection at 220 nm; 25° C.).

N-α-(benzyloxycarbonyl)-L-γ-glutamyl-L-cysteinyl-2-phenyl-(2R)-glycine, 2A

A 12-L, three-neck, jacketed round-bottom flask equipped with nitrogen purge, an overhead mechanical stirrer, a thermometer, and a pressure-equalizing addition funnel, was charged with N-α-(benzyloxycarbonyl)-L-γ-glutamyl-S-triphenylmethyl-L-cysteinyl-2-phenyl-(2R)-glycine (900 g×93.7% purity, 843.3 g, 1.11 mol) and toluene (3.6 L). After nitrogen purge, this was stirred, and trifluoroacetic acid (824 mL, 11.1 mol) was added. Poly(methylhydrosiloxane) (270 g) was added over 1 hour, maintaining the temperature at 25° C., and the reaction mixture stirred for an additional 17 hours. The reaction was then quenched by the addition of 1:1 heptane/methyl tert-butyl ether (5.4 L) over 1.5 hours, precipitating N-α-(benzyloxycarbonyl)-L-γ-glutamyl-L-cysteinyl-2-phenyl-(2R)-glycine. After an additional 2 hours stirring, the mixture was filtered, and the precipitate washed with heptane (3.6 L) and dried under vacuum at 40° C.

N-α-(benzyloxycarbonyl)-L-γ-glutamyl-L-cysteinyl-2-phenyl-(2R)-glycine. Exact mass: 517.15; MS (API-ES$^+$): m/z 518 (M+H$^+$); $^1$H NMR (400 MHz, DMSO-$d_6$): δ 8.78 (1H, d, j=7.2 Hz, NH), 8.09 (1H, d, J=8.0 Hz, NH), 7.62 (1H, d, J=8.0 Hz, NH), 7.36 (8H, m), 7.21 (2H, m), 5.35 (1H, d, J=7.6 Hz), 5.03 (2H, s), 4.56 (1H, m), 3.98 (1H, m), 2.68 (1H, m), 2.61 (1H, m), 2.26 (2H, m), 2.02 (1H, m), 1.78 (1H, m).

N-α-(benzyloxycarbonyl)-L-γ-glutamyl-3-[[2-[[bis [bis (2-chloroethyl)amino]phosphinyl]oxy]-ethyl]thio]-L-alanyl-2-phenyl-(2R)-glycine, 3A A 12-L, three-neck jacketed round-bottom flask equipped with nitrogen purge, an overhead mechanical stirrer, a thermometer, and a pressure-equalizing addition funnel, was charged with sodium hydroxide (49.46 g, 1.24 moo and methanol (1.99 L), which were stirred under nitrogen until dissolved, and then cooled to approximately 5° C. N-α-(benzyloxycarbonyl)-L-γ-glutamyl-L-cysteinyl-2-phenyl-(2R)-glycine (398.5 g×80.3% purity, 320 g, 0.62 mol) was added, followed by 2-(4-bromobenzenesulfonyloxy)ethyl N,N,N',N'-tetrakis (2-chloroethyl) phosphorodiamidate (1487.5 g×63.3% purity, 941.6 g, 1.55 mol) as an approximately 1 M solution in toluene. Under nitrogen, a solution of sodium hydroxide (56.88 g, 1.42 mol) in methanol (1.99 L) was added over 5 hours while maintaining the temperature of the reaction mixture at 5° C., and the reaction mixture was then stirred at that temperature for an additional 17 hours. While maintaining cooling, water (1.12 L) was added, the pH of the reaction mixture was adjusted to 6.9 with 1 M phosphoric acid, toluene (1.92 L) was added, and water (2.72 L) was added. The reaction mixture was stirred, then the phases separated, and the toluene phase (containing excess 2-(4-bromobenzenesulfonyloxy)ethyl N,N,N',N'-tetrakis (2-chloroethyl) phosphorodiamidate) removed. The aqueous layer was washed with toluene (1.92 L), the phases separated, and the toluene phase removed. The aqueous layer was then distilled under vacuum to remove methanol, maintaining the batch temperature below 35° C. Isopropyl acetate (1.6 L) was then added, the pH adjusted to 6.9, the phases separated, and the isopropyl acetate phase (containing 2-(4-bromobenzenesulfonyloxy)ethyl N,N,N',N'-tetrakis (2-chloroethyl) phosphorodiamidate) removed. Isopropyl acetate (3.2 L) was added, the pH adjusted to 4.8-4.85, the phases separated, and the isopropyl acetate phase (containing the N-α-(benzyloxycarbonyl)-L-γ-glutamyl-3-[[2-[[bis[bis(2-chloroethyl) amino]-phosphinyl]oxy]ethyl]thio]-L-alanyl-2-phenyl-(2R)-glycine) retained. Isopropyl acetate (0.64 L) was added to the aqueous phase, the pH adjusted to 4.8-4.85, the phases separated, and the isopropyl acetate phase was combined with the previous pH 4.8-4.85 isopropyl acetate phase. Water (1.6 L) was added to the combined isopropyl acetate phases, the pH adjusted to 5.25-5.3, the phases separated, and the aqueous phase removed. The water wash was repeated and, after separation of the aqueous phase, the isopropyl acetate phase was distilled under vacuum to reduce the batch volume to about 3.15 L before further processing. N-α-(benzyloxycarbonyl)-L-γ-glutamyl-3-[[2-[[bis[bis(2-chloroethyl)amino]-phosphinyl]oxy]ethyl]thio]-L-alanyl-2-phenyl-(2R)-glycine can be isolated from the solution by removal of the solvent.

N-α-(benzyloxycarbonyl)-L-γ-glutamyl-3-[[2-[[bis[bis(2-chloroethyl)amino]phosphinyl]oxy]-ethyl]thio]-L-alanyl-2-phenyl-(2R)-glycine. Exact mass: 887.15; MS (API-ES$^+$): m/z 890, 888 (M+H$^+$); $^1$H NMR (400 MHz, DMSO-$d_6$): δ 8.93 (1H, d, J=7.8 Hz, NH), 8.13 (1H, d, J=8.6 Hz, NH), 7.60 (1H d, J=8.2 Hz, NH), 7.36 (10H, m), 5.35 (1H, d, J=7.8 Hz), 5.03 (2H, s), 4.66 (1H, m), 3.97 (3H, m), 3.68 (8H, m), 3.30 (8H, m), 2.76 (3H, m), 2.57 (1H, m), 2.25 (2H, m), 1.99 (1H, m), 1.76 (1H, m).

N-α-(benzyloxycarbonyl)-L-γ-glutamyl-3-[[2-[[bis bis(2-chloroethyl)amino]phosphinyl]oxy]ethyl]sulfonyl]-L-alanyl-2-phenyl-(2R)-glycine, 4A A 12-L, three-neck jacketed round-bottom flask equipped with nitrogen purge, an overhead mechanical stirrer, a thermometer, and a pressure-equalizing addition funnel, was charged with a solution of N-α-(benzyloxycarbonyl)-L-γ-glutamyl-3-[[2-[[bis[bis(2-chloroethyl)amino]phosphinyl] oxy]-ethyl]thio]-L-alanyl-2-phenyl-(2R)-glycine (442.6 g, 0.50 mol) in isopropyl acetate (2.65 L) from the previous step. A solution of 2K HSO$_5$.KHSO$_4$.K$_2$SO$_4$ (OXONE™) (663.9 g, 1.08 mol) in water (2.66 L) was added with stirring under nitrogen, maintaining the temperature at 20-30° C.; and the reaction mixture was stirred overnight to complete the oxidation. The aqueous phase was separated and removed, and the isopropyl acetate phase was washed three times with water (885 mL), testing the water for the presence of persulfates with starch/KI paper after each wash. Isopropyl acetate (2.65 L) was added to the isopropyl acetate phase, and the combined solution was then distilled to reduce the volume to approximately 1.77 L. Isopropyl acetate (1.77 L) was then added, and the solution tested by Karl Fischer titration to ensure that the water content was not more than 0.2%. The mixture was stirred overnight, and the precipitated N-α-(benzyloxycarbonyl)-L-γ-glutamyl-3-[[2-[[bis[bis(2-chloroethyl)-amino]phosphinyl]oxy]ethyl]sulfonyl]-L-alanyl-2-phenyl-(2R)-glycine was filtered and dried at 35° C.

N-α-(benzyloxycarbonyl)-L-γ-glutamyl-3-[[2-[[bis[bis(2-chloroethyl)amino]phosphinyl]oxy]-ethyl]sulfonyl]-L-alanyl-2-phenyl-(2R)-glycine. Exact mass: 919.14; MS (API-ES$^+$): m/z 924, 922, 920 (M+H$^+$); $^1$H NMR (400 MHz, DMSO-$d_6$): δ 8.81 (1H, d, J=7.4 Hz, NH), 8.41 (1H, d, J=8.2 Hz, NH), 7.61 (1H, d, J=8.2 Hz, NH), 7.36 (10H, m), 5.30 (1H, d, J=7.4 Hz), 5.03 (2H, s), 4.94 (1H, m), 4.25 (2H, m), 3.98 (1H, m), 3.68 (8H, m), 3.54 (3H, m), 3.33 (9H, m), 2.25 (2H, m), 1.99 (1H, m), 1.78 (1H, m).

Canfosfamide Hydrochloride

In a 2-L autoclave, palladium on carbon (5%, 26.25 g) in isopropyl acetate (350 mL) was pre-reduced by three cycles of nitrogen purging (vacuum, nitrogen, release) followed by three cycles of hydrogen addition (3.4 bar) and release, with the mixture stirred for 30 minutes after the last hydrogen addition, followed by another nitrogen purge. N-α-(benzyloxycarbonyl)-L-γ-glutamyl-3-[[2-[[bis[bis(2-chloroethyl)amino]phosphinyl]oxy]ethyl]sulfonyl]-L-alanyl-2-phenyl-(2R)-glycine (190.6 g×91.89% purity, 175 g, 190 mmol) was dissolved in isopropyl acetate (700 mL) and water (53.9 mL), and the solution added to the autoclave. The three-cycle nitrogen purge was repeated, followed by two cycles of hydrogen addition and release, then the autoclave was pressurized with hydrogen to 3.4 bar with hydrogen, heated to 30° C., and held at that temperature for 7.7 hours, monitoring the reaction for completion by HPLC. The reaction mixture was filtered through diatomaceous earth (CELITE™) to remove the catalyst, and the filter washed with isopropyl acetate (2×175 mL). The combined filtrate and washings were dehydrated by vacuum distillation and re-addition of isopropyl acetate, then re-concentrated to a final solution mass of 485.7 g. Dichloromethane (350 mL) was added to the solution, followed by the addition of hydrogen chloride gas (8.37 g), and dilution with methyl tert-butyl ether (858 mL). After stirring for 2.5 hours, the reaction mixture was filtered; and the canfosfamide hydrochloride residue was washed with methyl tert-butyl ether (2×576 mL) and dried at 55° C. under vacuum.

Canfosfamide hydrochloride. Exact mass 785.10; MS (API-ES$^+$): m/z 800, 788, 786 (M+H$^+$); $^1$H NMR (300 MHz, DMSO-d$_6$): δ 8.81 (1H, d, J=7 Hz, NH), 8.62 (1H, d, J=7 Hz, NH), 8.4 (2H, bs), 7.35 (5H, m), 5.31 (1H, d, J=7 Hz), 4.95 (1H, m), 4.36 (2H, J=6 Hz, q), 3.87 (1H, J=6 Hz, t), 3.66 (8H, m), 3.57 (3H, m), 3.31 (9H, m), 2.50 (1H, s), 2.35 (1H, m), 2.02 (2H, m).

Example 2

Cytotoxic activity of N-α-(benzyloxycarbonyl)-L-γ-glutamyl-3-[[2-[[bis[bis(2-chloroethyl)amino]phosphinyl]oxy]ethyl]sulfonyl]-L-alanyl-2-phenyl-(2R)-glycine, 4A This example illustrates the beneficial effect of N-α-(benzyloxycarbonyl)-L-γ-glutamyl-3-[[2-[[bis[bis(2-chloroethyl)amino]phosphinyl]oxy]ethyl]sulfonyl]-L-alanyl-2-phenyl-(2R)-glycine, compound 4A, against human cancer cell lines in vitro. These results are considered predictive of efficacy in human cancer chemotherapy, as other anticancer agents, such as canfosfamide, tested in these assays have shown anticancer activity in humans.

The human cancer cell lines HL-60 (promyeloid myelocytic leukemia) and MX-1 (breast carcinoma) were obtained from the National Cancer Institute, Bethesda, Md., U.S.A. The CellTiter-Glo assay kit was obtained from Promega Corporation, Madison, Wis., U.S.A, and was used in accordance with the manufacturer's directions. All assays were conducted in triplicate wells, with dimethyl sulfoxide (DMSO) solvent control. The extent of cell growth was expressed as a percentage of the signal from the solvent control wells.

Log-phase cells were trypsinized, collected by centrifugation, and resuspended in a small volume of fresh medium, and the density of viable cells was determined following Trypan Blue staining. Cells were diluted in fresh media (5×10$^3$ cells/mL for HL-60 and 3×10$^3$ cells/mL for MX-1 cells), Compound 4A (concentrations between 0.1 and 200 μM, dissolved in DMSO, 50 μL) added immediately after dilution to achieve a final DMSO concentration of 0.5%, then the suspensions added at 150 μL/well to 96-well plates, and incubated for several hours to allow attachment in the case of adherent cells. The cells were cultured for approximately three doubling times (3 days). The cells were then collected by centrifugation, and 100 μL of the culture supernatant was replaced by the CellTiter-Glo reagent. After incubation for 15 minutes at room temperature, and the plate was read with a luminometer. The activity of compound 4A, expressed as IC$_{50}$, against the cell lines was: HL-60, 2.2 μM, and MX-1: 34.6 μM. The compound is approximately as potent as canfosfamide in this assay.

Example 3

Formulation and Therapeutic Examples

A solid formulation for oral administration is prepared by combining the following:

| | |
|---|---|
| Compound 4A | 25.0% w/w |
| Magnesium stearate | 0.5% w/w |
| Starch | 2.0% w/w |
| Hydroxypropylmethylcellulose | 1.0% w/w |
| Microcrystalline cellulose | 71.5% w/w | and the mixture is compressed to form tablets or filled into hard gelatin capsules containing, for example, 250 mg of compound 4A. Tablets may be coated, if desired, by applying a suspension of a film-forming agent (for example, hydroxypropylmethylcellulose), pigment (for example, titanium dioxide), and plasticizer (for example, diethyl phthalate), and drying the film by evaporation of the solvent.

A formulation for IV administration is prepared by dissolving compound 4A, for example as a pharmaceutically acceptable salt, to a concentration of 1% w/v in phosphate-buffered saline; and the solution is sterilized, for example by sterile filtration, and sealed in sterile containers containing, for example, 250 mg of a compound of this invention.

Alternatively, a lyophilized formulation is prepared by dissolving compound 4A, again for example as a pharmaceutically acceptable salt, in a suitable buffer, for example the phosphate buffer of the phosphate-buffered saline mentioned above, sterilizing the solution and dispensing it into suitable sterile vials, lyophilizing the solution to remove the water, and sealing the vials. The lyophilized formulation is reconstituted by the addition of sterile water, and the reconstituted solution may be further diluted for administration with a solution such as 0.9% sodium chloride intravenous infusion or 5% dextrose intravenous infusion.

Compound 4A, diluted in 5% dextrose intravenous infusion, is administered intravenously over 30 minutes to a patient suffering from metastatic ovarian carcinoma at an initial dose of 100 mg/m$^2$; and this dose is increased to 250 mg/m$^2$, 500 mg/m$^2$, 750 mg/m$^2$, and 1000 mg/m$^2$. The compound is administered at 1-week intervals. The same dose escalation is administered at 2- and 3-week intervals to other patients suffering from the same cancer.

While this invention has been described in conjunction with specific embodiments and examples, it will be apparent to a person of ordinary skill in the art, having regard to that skill and this disclosure, that equivalents of the specifically disclosed materials and methods will also be applicable to this invention; and such equivalents are intended to be included within the following claims.

We claim:
1. A compound of the formula
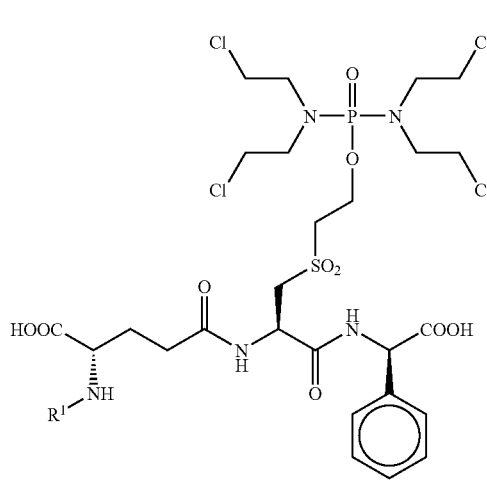
or its salt.
2. A composition comprising a compound of the formula
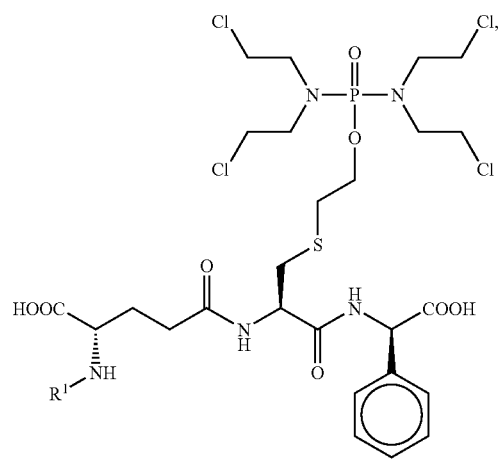
or its salt.
* * * * *

UNITED STATES PATENT AND TRADEMARK OFFICE
CERTIFICATE OF CORRECTION

| | | |
|---|---|---|
| PATENT NO. | : 8,198,247 B2 | Page 1 of 1 |
| APPLICATION NO. | : 11/018391 | |
| DATED | : June 12, 2012 | |
| INVENTOR(S) | : Boulanger et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 635 days.

Signed and Sealed this
Fifth Day of March, 2013

Teresa Stanek Rea
*Acting Director of the United States Patent and Trademark Office*